(12) United States Patent
Schon et al.

(10) Patent No.: US 6,515,187 B1
(45) Date of Patent: Feb. 4, 2003

(54) PROCESS FOR RECOVERING ACROLEIN OR PROPIONALDEHYDE FROM DILUTE AQUEOUS STREAMS

(75) Inventors: Steven Gabriel Schon, Strafford, PA (US); Samuel Marc Daniel, Malvern, PA (US); Richard Alan Sander, Maple Glen, PA (US)

(73) Assignee: Atofina Chemicals, Inc., Philadelphia, PA (US)

( * ) Notice: Subject to any disclaimer, the term of this patent is extended or adjusted under 35 U.S.C. 154(b) by 0 days.

(21) Appl. No.: 10/177,710

(22) Filed: Jun. 21, 2002

Related U.S. Application Data
(60) Provisional application No. 60/326,901, filed on Oct. 3, 2001.

(51) Int. Cl.⁷ ............................................... C07C 45/00
(52) U.S. Cl. ....................................................... 568/492
(58) Field of Search ......................................... 568/492

(56) References Cited

U.S. PATENT DOCUMENTS

| | | | |
|---|---|---|---|
| 3,433,840 A | 3/1969 | Shima et al. ................ | 260/604 |
| 3,927,153 A | 12/1975 | Tarhan ........................ | 261/128 |
| 4,110,370 A | 8/1978 | Engelbach et al. .......... | 260/530 |
| 4,234,519 A | 11/1980 | Yeoman et al. .............. | 568/492 |
| 5,326,916 A | 7/1994 | Kobayashi et al. .......... | 568/492 |
| 5,770,021 A | 6/1998 | Hego et al. ..................... | 203/8 |
| 6,166,263 A | 12/2000 | Etzkorn et al. ........... | 568/469.9 |

*Primary Examiner*—Alan Siegel
(74) *Attorney, Agent, or Firm*—Gilbert W. Rudman (57) ABSTRACT

A method of purifying acrolein or propionaldehyde with a single column distillation system is provided, where the distillation system has a side-draw take-off outlet for recovering purified acrolein or propionaldehyde located between the crude product feed point and the light-boiling impurities distillation site.

22 Claims, 5 Drawing Sheets

PROCESS FOR RECOVERING ACROLEIN OR PROPIONALDEHYDE FROM DILUTE AQUEOUS STREAMS

CROSS REFERENCE TO RELATED APPLICATION

This application claims the benefit of co-pending provisional application serial No. 60/326,901, filed Oct. 3, 2001, the entire disclosure of which is herein incorporated by reference.

FIELD OF THE INVENTION

This invention relates to the field of recovering and purifying compounds, in particular the purification of acrolein or propionaldehyde, from a dilute aqueous solution containing impurities.

BACKGROUND OF THE INVENTION

Acrolein and propionaldehyde are important industrial chemicals useful in a variety of organic syntheses. For example, acrolein may be reacted with methyl mercaptan to form beta-methylthiopropionaldehyde (MTPA).

Acrolein is conventionally produced by the vapor-phase oxidation of propylene over a solid-phase catalyst. This reaction produces a gaseous mixture containing acrolein, gases (e.g., nitrogen, oxygen, carbon monoxide, and carbon dioxide), propylene, water, and reaction by-products such as acrylic acid, acetic acid, formic acid, formaldehyde, acetaldehyde, allyl alcohol and polymers resulting from the degradation of acrolein.

Typically, acrolein is purified from the reaction effluent gases by absorption into water, resulting in a dilute aqueous acrolein stream (typically less than 5% acrolein) that also contains light-boiling reaction byproduct impurities such as formaldehyde, acetaldehyde, propionaldehyde, allyl alcohol and acetone. The crude, dilute aqueous acrolein produced in the absorption step is then subjected to distillation to separate the acrolein/water azeotrope. Present purification methods, which are well-known in the art, involve the multi-column distillation of the crude acrolein solution to recover relatively pure product. See, for example, U.S. Pat. No. 3,433,840 of Takesaburo et al.

A typical multi-column distillation for acrolein recovery has three columns, and operates as follows: A concentration column ($1^{st}$ column) separates concentrated crude acrolein as an overhead distillate product, with the water and heavier-boiling impurities going to the bottom of the column. The water may be recycled. The acrolein distillate (typically more than 92 wt % pure) is at or near its azeotropic water content, and contains light-boiling impurities such as acetaldehyde.

The acrolein distillate from the first column is then sent to a "lights" removal column ($2^{nd}$ column), which separates light-boiling impurities, especially acetaldehyde, as a distillate product. The lights-depleted concentrated acrolein then goes "to the bottoms"; i.e., falls to the bottom of the lights removal column for passage to the next column.

Note that acetaldehyde cannot be efficiently separated from the acrolein before passage through the concentration column, because acetaldehyde has too high an affinity for water. It is known that an acetaldehyde distillate isolated upstream of the concentration column contains significant amounts of acrolein, representing an undesirable acrolein recovery loss.

After passing through the lights-removal column, the lights-depleted acrolein concentrate (also called the "lights column bottoms") is sent to a product column ($3^{rd}$ column), where purified acrolein is taken as a distillate product, and heavy impurities and acrolein degradation products are removed from the column bottoms. A fraction of the acrolein is lost to the bottoms of the column, due both to limitations on the separation and the formation of thermal degradation products (e.g., acrolein dimer and polymer formation; see below).

Optionally, the product column may be operated as an extractive distillation, whereby an intermediate-boiling solvent is added to the column. The solvent goes to the bottom of the recovery column, diluting and reducing the boiling temperature of the lower portion of the column. The "solvent/heavies" bottoms stream is sent to a solvent recovery column, where the solvent is taken as a distillate product and recycled to the purification column. The heavy-boiling impurities and thermal degradation products are removed via the bottoms. Depending on the solvent chosen, additional water removal (to below the normal acrolein azeotropic composition) may be achieved.

Although widely used, multi-column distillation methods for recovery of acrolein have number of significant cost and operational disadvantages.

For example, the multiple columns and supporting apparatus required for this process represent a major capital investment for a commercial acrolein production facility. It is also expensive to maintain a multiple distillation column system.

Moreover, each column in the multi-column system cannot achieve perfect separation, and thus there is a cumulative acrolein recovery loss of up to several percent due to separations losses in each distillation step.

Also, acrolein is a thermally-sensitive monomer which forms cyclic dimers and linear polymers on exposure to heat. These dimers and polymers are referred to herein as "thermal degradation products." The amount of thermal degradation products formed in any system follows certain non-linear functions with respect to temperature and acrolein concentration/residence time in the distillation system (the function is exponential with respect to temperature; and "power-law" with respect to concentration/residence time). Thus, higher temperatures or extended residence times in a distillation system results in excessive production of thermal degradation products.

The thermal degradation products are insoluble, and may foul the internal workings and heat exchangers of distillation equipment. Excessive production of thermal degradation products during distillation necessitates frequent shut-down and cleaning of the distillation equipment, resulting in lost production and high maintenance costs. Furthermore, any thermal degradation products formed represent an unrecoverable acrolein yield loss, which translates into an economic penalty for the acrolein manufacturer.

During multi-column distillation, acrolein is repeatedly exposed to high temperatures and experiences relatively long residence times in the columns.

Thus, significant production of thermal degradation products occurs, resulting in unrecoverable yield losses and rapid fouling of the distillation system.

Production of thermal degradation products may be reduced by the addition of acrolein polymerization inhibitors (e.g., hydroquinone, phenothiazine, and derivatives of hydroquinone or phenothiazine) to the distillation system. As the thermal degradation products may form at any stage of the distillation process, polymerization inhibitors must be added to the top of each column in a multi-column distillation system. Moreover, unreacted polymerization inhibitors are lost to the heavy bottoms byproduct, and may ultimately contaminate the acrolein product. The use of polymerization inhibitors in a multi-column distillation system can therefore represent a significant operating cost for acrolein manufacturers.

Propionaldehyde has vapor-liquid equilibrium (VLE) and chemical properties nearly identical to acrolein. Purification of this compound by multi-column distillation has similar drawbacks as described above for acrolein.

What is needed, therefore, is a method of purifying acrolein or propionaldehyde which can be accomplished with less equipment (and thus less capital costs), which allows efficient product recovery without the separation losses inherent in multi-column systems, and which uses lower temperatures and residence times so as to reduce formation of thermal degradation products.

SUMMARY OF THE INVENTION

It has been unexpectedly found that purified acrolein or propionaldehyde can be recovered from a single distillation column through at least one liquid side-draw take-off outlet positioned between the crude product feed point and the distillation site for light-boiling impurities. The purified product is surprisingly free of light-boiling point contaminants. It is therefore an object of the present invention to provide a method for purifying acrolein or propionaldehyde, comprising the steps of:

1) providing a dilute aqueous solution comprising acrolein or propionaldehyde and light-boiling point impurities;
2) providing a single column distillation system, comprising:
   i. a distillation column having a top condenser;
   ii. a crude product feed inlet on the distillation column;
   ii. a distillation site for the light-boiling point impurities above the crude product feed inlet;
   iii. a liquid side-draw take-off outlet for recovering purified acrolein or propionaldehyde located between the crude product feed inlet and the distillation site for the light-boiling point impurities; and
   iv. a take-off point for the removal of water and heavy impurities below the product feed inlet;
3) introducing the dilute aqueous solution into the distillation column through the crude product feed inlet so as to distill the dilute aqueous solution;
4) recovering purified acrolein or propionaldehyde through the liquid side-draw take-off outlet; and
5) optionally recovering water, substantially free of acrolein or propionaldehyde through the lower outlet.

In a preferred embodiment, a portion of the water from the bottom outlet is recycled for use elsewhere in the process, e.g., in the absorption of acrolein, to produce the aqueous feed to the column. Preferably, the recovered purified product is acrolein.

In one aspect of the invention, the single-column distillation system is operated under a partial vacuum. Preferably, the system is operated at a partial pressure of about 400 to about 650 mm (absolute), more preferably at a pressure of about 590–650 mm Hg (absolute), at the side-draw stage.

In another aspect of the invention, the single column distillation system further comprises one or more internal or external vapor partial condensers, intermediate between the liquid side-draw take off and the top condenser.

In yet another aspect of the invention, the single column distillation system further comprises one or more separation stages, for example a stripping section, a rectifying section, and a lights-removal section.

In a still further aspect of the invention, the method for purifying acrolein or propionaldehyde further comprises the step of adding at least one polymerization inhibitor to the single column distillation system. In one embodiment, polymerization inhibitor is added at a point below the side-draw take-off outlet, but above the dilute aqueous solution feed. In another embodiment, polymerization inhibitor is added to the single column distillation system at a point above the side-draw take-off outlet, wherein the inhibitor is compatible with the end-uses of the acrolein or propionaldehyde product.

All percentages expressed herein are weight percent values.

DETAILED DESCRIPTION OF THE INVENTION

The present invention is directed to a method of purifying acrolein (2-propenal; $CH_2=CHCHO$; CAS Reg. No. 107-02-8) or propionaldehyde (propanal; $CH_3CH_2CHO$; CAS Reg. No. 123-38-6) with a single column distillation system. The single column distillation system comprises a side-draw take-off outlet for recovering purified acrolein or propionaldehyde, which is located between a crude product feed point and a light-boiling impurities distillation site in the column.

As used herein, "light-boiling impurities" means any material (other than an acrolein/water or propionaldehyde/water azeotrope) that is present in a crude dilute aqueous solution of acrolein or propionaldehyde, and which has a boiling point less than or equal to acrolein or propionaldehyde. For example, light-boiling impurities are those materials whose composition relative to acrolein or propionaldehyde is enriched (higher concentration) in the vapor phase compared to the liquid composition in equilibrium with the vapor. Light-boiling impurities include, for example, formaldehyde, acetaldehyde, carbon dioxide, propylene, propane, and oxygen.

As used herein, "heavy-boiling impurities" means any material (other than an acrolein/water or propionaldehyde/water azeotrope) that is present in a crude dilute aqueous solution of acrolein or propionaldehyde, and which has a boiling point greater than or equal to acrolein or propionaldehyde. For example, heavy-boiling impurities are those materials whose composition relative to acrolein or propionaldehyde is depleted (lower concentration) in the vapor phase compared to the liquid composition in equilibrium with the vapor. Heavy-boiling impurities include, for example, allyl alcohol, acetone, acrylic acid, water, and polymerization inhibitors.

Side-draw configurations for recovering acrolein or propionaldehyde have not heretofore been used in distillation systems that did not use an additional solvent or entrainer, as it was believed that light-boiling impurities would be drawn out along with the product as they pass the side-draw point, providing an impure product. Thus, acrolein or propionaldehyde has typically been recovered as a distillation overhead or bottoms product. Also, to achieve the desired level of purity, multiple-column distillations of acrolein or propionaldehyde are usually performed.

It has now unexpectedly been found that purified acrolein or propionaldehyde may be recovered through a side-draw take-off outlet in a single column distillation system, without appreciable contamination from light-boiling impurities. This is achieved even though the side draw is positioned in the distillation column below the distillation site for the light-boiling impurities. Thus, a single column distillation system may be conveniently used to purify acrolein and propionaldehyde from crude dilute aqueous solutions.

As used herein, the "light-boiling impurities distillation site" is that part of the distillation column in which the light-boiling impurities are separated. As used herein, the "heavy-boiling impurities distillation site" is that part of the distillation column in which the heavy-boiling impurities are separated.

As used herein, "purify" or "purified" indicates a product that is at least 95% pure, with no more than 1% light-boiling impurities and no more than 4% water, preferably at least 96% pure, with no more than 0.4% light-boiling impurities and no more than 3.0% water, and more preferably at least 97% pure, with no more than 0.2% light-boiling impurities and no more than 2.6% water.

The single column distillation system of the invention achieves high overall recoveries of product, with minimal losses due to separation inefficiencies and formation of thermal degradation products. The system is also less complex and uses less equipment than conventional multi-column distillation processes, and therefore has significantly lower operational costs, and fewer maintenance and auxiliary chemical requirements.

The use of the single column distillation system also avoids the excessive formation of thermal degradation products, as the acrolein is not exposed to the relatively high temperatures, concentrations, and residence times encountered in the bottoms/reboiler of conventional multi-column distillation systems. Thermal degradation recovery losses and fouling rates are therefore greatly reduced. Furthermore, less polymerization inhibitors are needed, as the inhibitors need only be added to a single column. This significantly reduces the operating costs associated with the adding the inhibitors.

In the present system, polymerization inhibitors may be fed into the column at points below the side-draw product take-off outlet. Unused inhibitor will fall to the column bottoms, and will not be drawn off with the purified acrolein product. This offers the potential for improved operation and reduced maintenance of the lower (hotter and hence more fouling-prone) section of the column through improved fouling inhibition, without risk of compromising acrolein product quality.

Polymerization inhibitors injected below the side-draw take-off outlet thus do not need to be compatible with the end-uses of the side-draw product. Provided that the inhibitor is substantially non-volatile and is injected at a point sufficiently below the side-draw take-off outlet to ensure that substantially no inhibitor is entrained into the side-draw take-off outlet.

Polymerization inhibitors which are acceptable for use with the purified product may be added above the product side-draw take-off outlet, e.g., into the condenser or reflux, as is practiced in conventional acrolein distillation systems. For example, liquid polymerization inhibitor solution may be sprayed into the vapor inlet of a distillation column condenser. Such compatible polymerization inhibitors may be used in place of, or in addition to, those added below the side-draw take-off point.

Suitable polymerization inhibitors include, but are not limited to, inhibitors comprising hydroquinone (HQ) and derivatives of HQ (e.g., the methyl ether of HQ) and inhibitors comprising phenothiazine (PTZ) and derivatives of PTZ. For example, the polymerization inhibitor may comprise HQ, PTZ or their derivatives dissolved in acrolein. The polymerization inhibitor may also comprise mixtures of HQ, PTZ, and/or their derivatives.

As discussed above, propionaldehyde has a vapor-liquid equilibrium and chemical properties which are nearly identical to acrolein. Thus, it is apparent that the present method may also be used to recover and purify propionaldehyde. For ease of illustration, however, the invention is discussed below in terms of purifying acrolein.

Conventional acrolein synthetic processes produce a gaseous product containing acrolein and other organic impurities. This gaseous product is absorbed into water to form an acrolein/water azeotrope that can be separated from light-boiling point impurities by distillation.

For example, the gaseous product from the gas-phase catalytic oxidation of propylene can be absorbed into water to give a crude dilute (i.e., less than 5%) aqueous acrolein solution, that also contains light-boiling reaction byproduct impurities such as formaldehyde, acetaldehyde, carbon dioxide, propylene, propane, and oxygen, as well as heavy boiling impurities such as allyl alcohol, acrylic acid and acetone. Dilute acrolein solutions suitable for purification by the present method may also be obtained from other sources.

In the practice of the present invention, a crude dilute acrolein solution is introduced into a single column distillation system configured for distilling acrolein. It is within the skill in the art to choose the size and configuration of the system components for the separation of acrolein from the dilute solution. The system must have a side-draw take-off outlet for removing purified acrolein located between the crude product feed and the light-boiling impurities distillation site.

The location of the crude product feed and side-draw take-off points is not critical, as long as these components are located between the column bottoms and top distillate take-offs. Within these parameters, one of ordinary skill in the art may easily determine the precise location of these components that is consistent with achieving the target acrolein purity. The side-draw take-off outlet, however, must be above the crude product feed point.

The single column distillation system of the invention may be operated below, at, or above atmospheric pressure. Operation of the single column distillation system under partial vacuum allows recovery of purified acrolein product with a reduced water content. Typically, acquiring a reduced water content acrolein product requires solvent-assisted (extractive) distillation. Also, lower internal (stage) temperatures may be used when the system is operated under partial vacuum, which reduces the rate of thermal degradation product formation and its associated fouling.

In one embodiment, the distillation column is operated at atmospheric pressure (i.e., 760 mm Hg (absolute)) as measured at the top of the column. In a preferred embodiment, the system is operated under partial vacuum. When operating the column at below atmospheric pressure, sufficient vacuum should be applied so that the side-draw take-off outlet is in an area of below-atmospheric pressure, for example from about 400 to about 650 mm Hg (absolute) as measured in the vapor space at the side-draw take-off outlet. Preferably, the distillation column is operated at about 590 to about 650 mm Hg (absolute) as measured in the vapor space at the side-draw take-off outlet.

It is understood that the pressure inside the distillation column increases from top to bottom, and thus the pressure at the side-draw take-off outlet may not be the same as the pressure measured at the top of the column. In smaller single-column distillation systems, this pressure differential is not large (e.g., approximately 2–3 mm Hg (absolute) for the entire column). The pressure differential along the distillation column in commercial single-column distillation systems may be more significant. For example, the pressure increase in commercial columns may be estimated as approximately 3–5 mm Hg (absolute) per tray for trayed columns, and 1–15 mm Hg (absolute) per foot of packing depth for packed columns.

Figure 1:
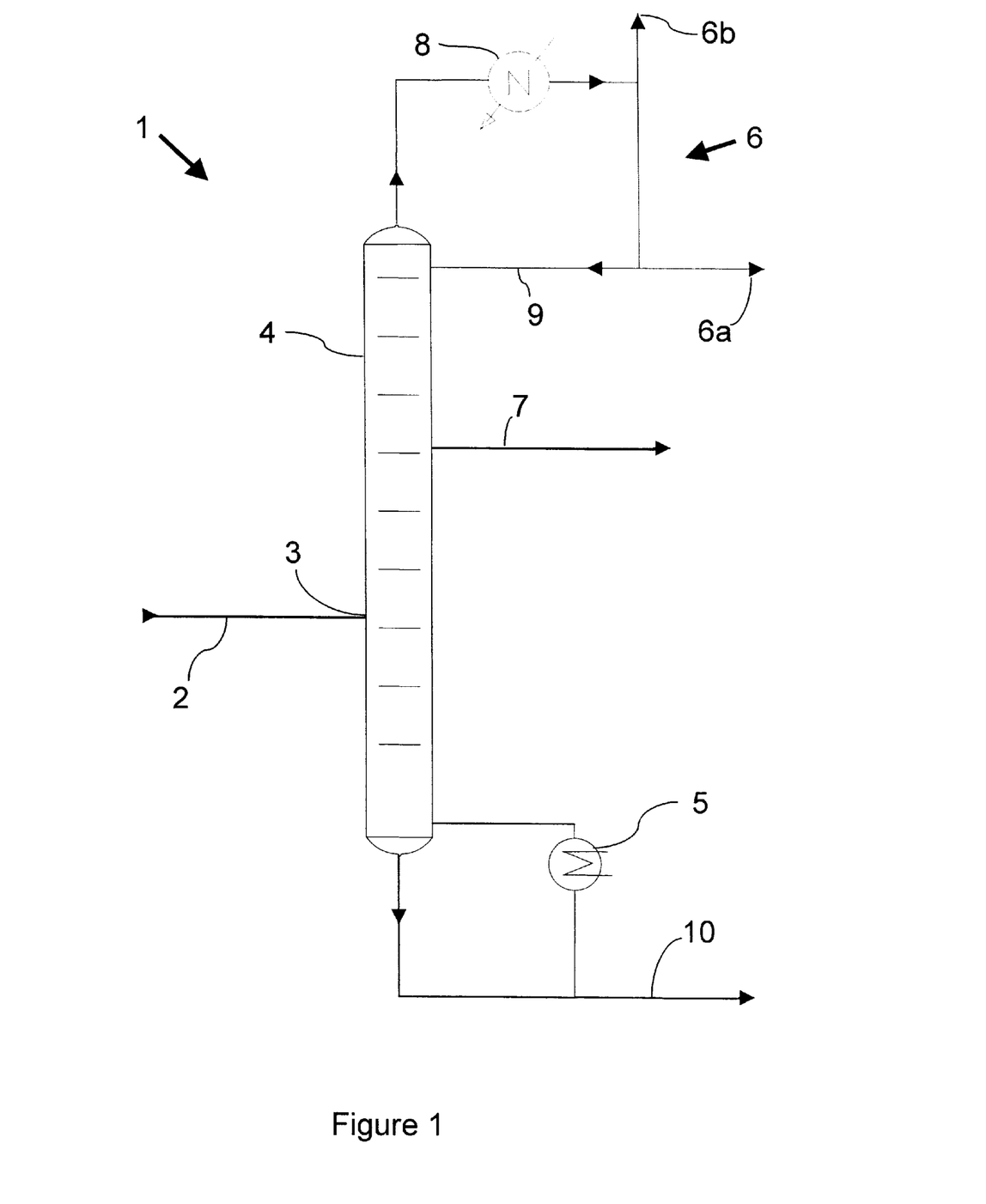
FIG. 1 is a schematic of a basic single-column distillation system of the invention, showing the liquid side-draw take-off outlet.

A single column distillation system of the invention severally designated 1 is shown in FIG. 1. In the present method, a crude dilute aqueous solution containing acrolein and light-boiling impurities is introduced from source 2 into distillation column 4 through a crude product feed inlet 3, which is typically located near the bottom of the column. Preferably, the distillation column has a smaller diameter above the feed point than below the feed point, consistent with good design practice to avoid flooding of the column sections.

The crude acrolein solution is heated to boiling by heating element 5 located at the bottom of distillation column 4. For example, the crude dilute acrolein solution may be heated to between about 99 and 110° C., preferably about 99.5° C. However, the precise temperature required to boil the solution may vary. Heating element 5 may comprise any component or system designed to impart heat to a distillation column, such as are known in the art. For example, heating element 5 may comprise a conventional reboiler, internal heating coil, heating jacket or mantle, or live-steam injection apparatus. In one embodiment, the reboiler may be of the forced-circulation design, to ensure high velocities and minimize fouling deposits. Preferably, heating element 5 comprises a reboiler heated by heating media that is no more than 20° C. hotter than the bubble point temperature of the aqueous heavy-boiling take-off stream. This minimizes the "skin" temperature of the reboiler, which in turn reduces the rate of polymerization and fouling of the reboiler by heavy impurities such as allylic alcohol and acrylic acid.

Boiling the crude acrolein solution causes the solution to partially vaporize and travel up the distillation column, where the components of the solution are separated from each other. Acrolein is recovered as a liquid through a liquid side-draw take-off outlet 7 located between crude product feed point 3 and light-boiling impurities distillation site 6. Light-boiling impurities travel past the side-draw take-off outlet, are partially or totally condensed by a condenser 8, and are collected at the light-boiling impurities distillation site 6. A portion of the condensed light-boiling impurities is returned to the top of the column 4 as reflux 9. Water and heavy-boiling impurities are withdrawn from the column bottom take-off 10.

Side-draw take-off outlet 7 comprises any outlet suitable for removing material from distillation column 4, and may include any component or apparatus for this function as is well known in the art; for example, control valves, pumps, solenoids with timers, etc. Preferably, distillation column 4 is fitted with one side-draw take-off outlet 7.

Light-boiling impurities distillation site 6 may be located in any component or apparatus designed to fully or partially condense and remove light-boiling impurities from the distillation column; (e.g., acetaldehyde, formaldehyde, propylene, propane, and oxygen) in addition to providing liquid reflux to the top of the column. Such components or apparatuses are well-known in the art. The light boiling impurities may exit the system as a liquid 6a and/or as a vapor distillate stream 6b.

Distillation column 4 may comprise one or more separation stages, as long as the minimum number required to achieve a target acrolein purity are present. One of ordinary skill in the art is able to determine the minimum number and type of separation stages required to achieve target purity. For example, the distillation system may comprise a stripping stage, a rectifying stage, and a light-boiling impurities distillation stage.

Distillation column 4 may also comprise one or more internal mass-transfer devices designed to provide the required number of theoretical plates to achieve a target acrolein purity. One of ordinary skill in the art is able to determine the requisite number of theoretical plates for a given target purity. Suitable internal mass-transfer devices include, but are not limited to, discrete perforated trays (e.g., sieve trays, valve trays, bubble-cap trays, counter-current flow trays, etc.), and packings (e.g., rings, saddles, tellerettes, structured packings, etc.). Preferred mass-transfer devices are perforated trays with fixed openings, such as sieve trays, Dual-Flow and Ripple® trays and corrugated structured packings, such as Flexipac® packing manufactured by Koch-Glitsch, Wichita, Kans., and Sulzer packings manufactured by Sulzer Chemtech USA, Inc., Deer Park Tex. 77536.

In one embodiment of the invention, the internal mass-transfer devices may comprise perforated-hole fractionation trays without moving parts, said holes being at least ½" in diameter, to tolerate fouling. Examples of suitable trays include, but are not limited to: sieve trays with downcomers; oriented fixed valve trays with downcomers; Dual-Flow trays without downcomers; and Ripple® trays without downcomers.

The internal mass transfer devices may also comprise corrugated structured packing, with spacing between the packing sheets of least ½", to minimize column height and pressure drop, and to tolerate fouling.

Preferably, the internal mass transfer devices have polished surfaces to minimize the adherence of fouling deposits. In another preferred embodiment of the invention, the internal mass-transfer devices have surfaces coated with, or composed entirely of, fluoropolymer materials. Such fluoropolymer materials are known to be chemically resistant to the chemical species within the column, and have non-stick properties, both of which minimize the adherence of fouling deposits.

The distillation column may also comprise internal mass-transfer devices assembled into removable cartridges, to facilitate rapid replacement and restoration of operations, for example while the removed cartridges are cleaned off-line.

It is apparent that the single column distillation system described above may comprise additional components or configurations consistent with achieving the target purity of acrolein. One of ordinary skill in the art is familiar with such additional components or configurations.

For example, the distillation column may be operated with either total or partial condensers; i.e., with one or more liquid or vapor light-boiling distillate take-offs. For example, the distillation column may be fitted with one or more vapor partial condensers located between the side-draw take-off outlet and the top distillate. Such condensers will facilitate the use of inexpensive cooling media (e.g., cooling water or air) for the majority of the required column reflux, and thus minimize the top reflux flow, which typically requires expensive refrigeration for the top condenser.

In one embodiment, the distillation column may comprise an intermediate partial condenser (internal or external) between the side-draw and the light-boiling impurities distillation site. Optionally, the column has a smaller diameter above the intermediate partial condenser, consistent with good design practice, to avoid flooding of the column sections.

In one embodiment, the intermediate partial condenser is internal to the column, and may comprise a tubular heat exchanger which is cooled with a non-refrigerated cooling medium. In this arrangement, a portion of the vapor rising through the internal intermediate partial condenser is condensed and drains back to the stage below the condenser, while the remaining vapor rises to the stage above the condenser. Simultaneously, down-coming liquid from the stage above the condenser, optionally containing polymerization inhibitors, enters the top of the condenser tubes and joins with the condensing liquid to inhibit the formation of fouling polymers within the condenser tubes. The internal intermediate partial condenser is preferably located at a stage as close as practically possible to the light-boiling impurities distillation site, as long as the stage vapor temperature remains above the inlet temperature of non-refrigerated cooling media (e.g., cooling water or air).

Figure 2:
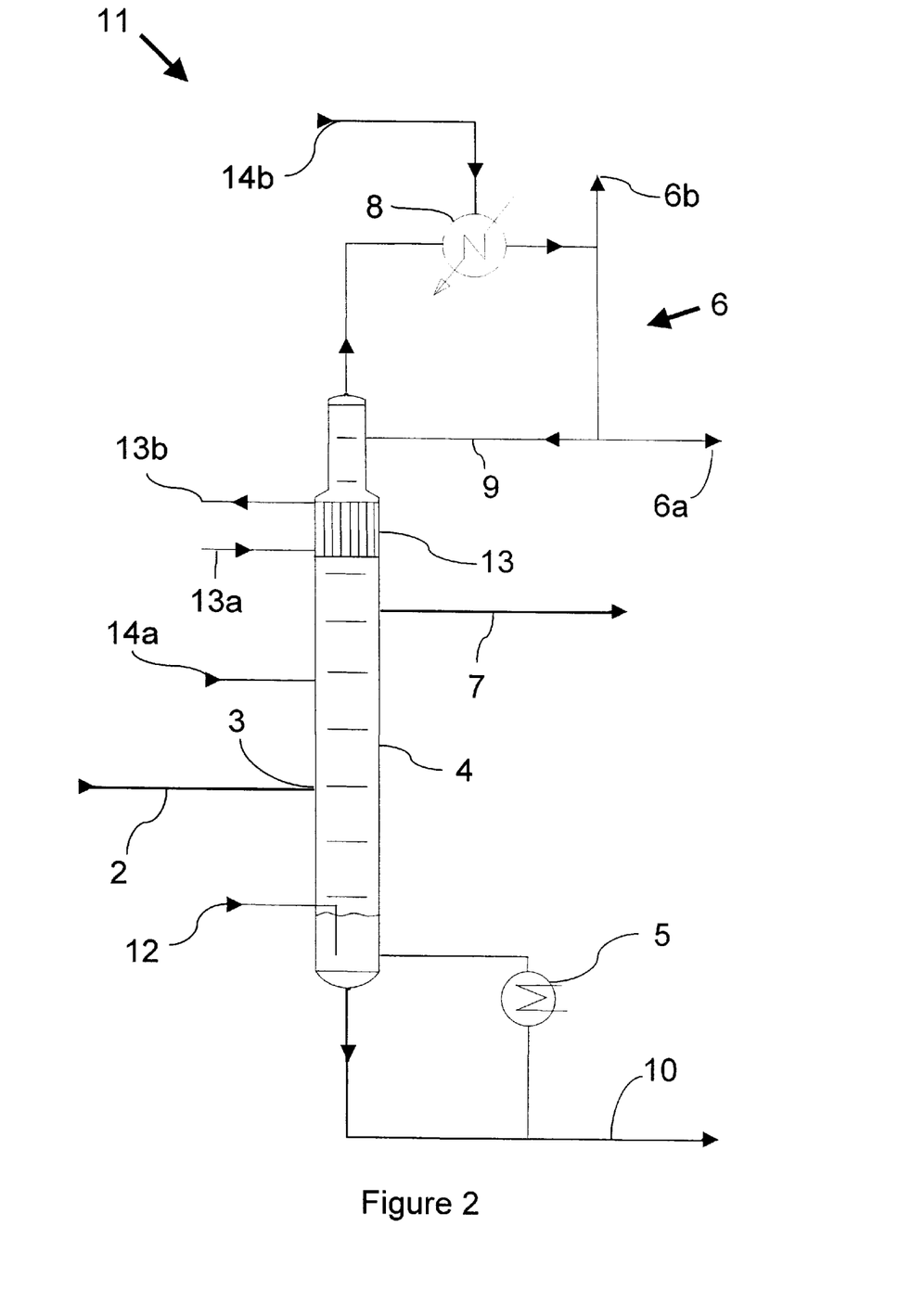
FIG. 2 is a schematic of a single-column distillation system of the invention with an internal intermediate condenser.

A preferred single column distillation system comprising an internal intermediate partial condenser, severally designated 11, is shown in FIG. 2 where like numbers designate structures in common with FIG. 1. Crude dilute aqueous solution containing acrolein and light-boiling point impurities is introduced into distillation column 4 from source 2 via crude product feed inlet 3. The crude acrolein solution is heated to boiling by heating element 5, and by the optional live steam sparge 12. The partially vaporized crude aqueous solution travels up the distillation column for separation. Acrolein is recovered through side-draw take-off outlet 7. Vapor containing light-boiling point impurities rises past side-draw take-off outlet 7 and travels through internal intermediate partial condenser 13, which is located one or more stages below light-boiling point impurities distillation point 6. The intermediate partial condenser 13 is preferably located at a sufficiently low stage such that the vapor entering the condenser is at a higher temperature than the cooling media to the intermediate partial condenser 13. Light-boiling impurities are partially or totally condensed in condenser 8, which is cooled by refrigerated cooling media, and a portion of the light-boiling impurities are returned to the column as reflux 9. The remaining light boiling point impurities exit the column as liquid 6a or vapor distillate stream 6b.

Non-refrigerated cooling media is circulated through internal intermediate partial condenser 13 via inlet 13a and outlet 13b. A portion of the vapor is condensed in internal intermediate partial condenser 13 drains back to 10 the stage below the condenser, while the remaining vapor rises to the stage above the condenser. The diameter of distillation column 4 above internal intermediate partial condenser 13 is smaller than that of the rest the column. As before, water and heavy boiling impurities are withdrawn from the column bottom take-off outlet 10.

Polymerization inhibitors are added to the distillation column at feed points 14a and 14b. The inhibitors added through feed point 14a, which is above crude product feed inlet 3 but below side-draw take-off outlet 7, may include inhibitors not compatible with the intended end use of the purified product. However, the inhibitors added through feed point 14b, which enters the top of the condenser 8 in light-boiling point impurities distillation point 6, must be compatible with the intended product end use. This is because the inhibitors added through feed point 14b join with the condensing liquid returned to the column above side-draw take-off outlet 7, and distribute between the purified product and the liquid that goes down the column below the side-draw point.

In another embodiment, the distillation column comprises an external intermediate partial condenser, located at a stage intermediate between the side-draw take-off outlet and the light-boiling impurities distillation site. In operation, a portion of the vapor in the distillation column is withdrawn into the intermediate external partial condenser, condensed by a heat exchanger cooled with a non-refrigerated cooling medium, and returned as a side reflux stream to the stage immediately below the side-draw take-off outlet. Liquid polymerization inhibitor solution may be sprayed into the vapor inlet of the condenser, to minimize the fouling of the condenser surfaces. It is preferred that the vapor be drawn into the intermediate external partial condenser at a stage as close as practically possible to the light-boiling impurities distillation site, as long as the stage vapor temperature remains above the inlet temperature of non-refrigerated cooling media (e.g., cooling water or air).

In one embodiment, the external intermediate partial condenser may be mounted at grade with a standard accumulator (i.e., reflux drum) and reflux return line. This arrangement is represented in FIG. 3, where like numbers designate structures in common with FIGS. 1 and 2.

Figure 3:
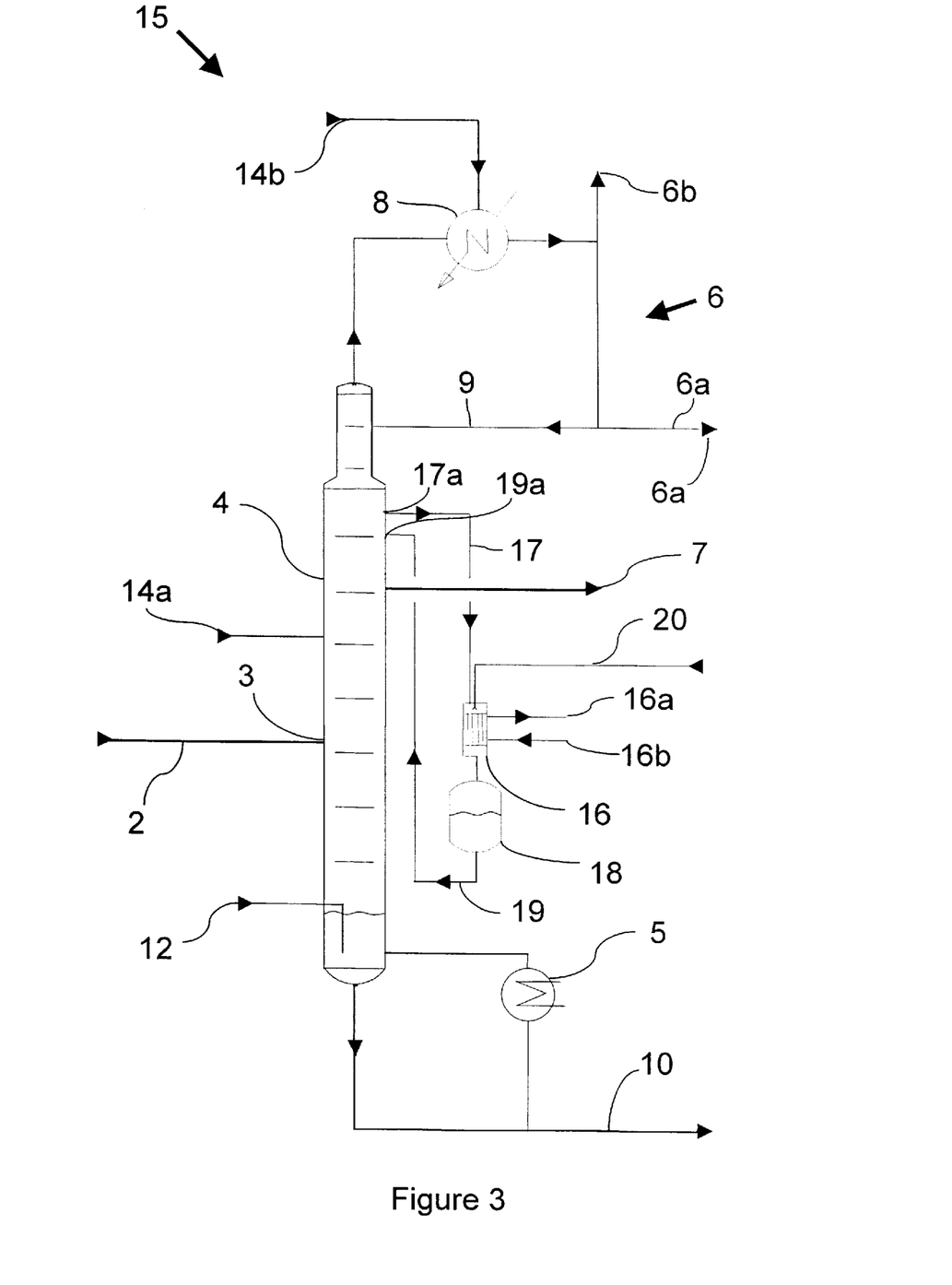
FIG. 3 is a schematic of a single-column distillation system of the invention having a conventional side external partial condenser with a reflux drum.

Referring to FIG. 3, a single column distillation system comprising an external intermediate partial condenser with a reflux drum, severally designated 15, is shown. As before, crude dilute aqueous solution containing acrolein and light-boiling point impurities is introduced into distillation column 4 from source 2 via crude product feed inlet 3. The crude acrolein solution is heated to boiling by heating element 5, and by the optional live steam sparge 12. The partially vaporized crude aqueous solution travels up the distillation column for separation. Acrolein is recovered through side-draw take-off outlet 7. However, a portion of the vapor which rises past side-draw take-off outlet 7 is drawn into external intermediate condenser 16 through draw 17, which exits the column at draw point 17a. The vapor is condensed and falls into intermediate reflux drum 18, where it is returned to distillation column 4 above side-draw take-off outlet 7 through return 19, which enters the column at return point 19a located near the liquid stage immediately below draw point 17a. External intermediate condenser 16 is cooled with non-refrigerated media via inlet 16a and outlet 16b.

Draw point 17a is located one or more stages below light-boiling point impurities distillation point 6. Draw point 17a is preferably located at a sufficiently low stage such that the vapor is at a higher temperature than the cooling media to the intermediate condenser 16. As before, light-boiling impurities are partially or totally condensed in condenser 8, which is cooled by refrigerated cooling media, and a portion of the light-boiling impurities are returned to the column as reflux 9. The remaining light boiling point impurities exit the column as liquid 6a or vapor distillate stream 6b. The diameter of distillation column 4 above draw point 17a is smaller than that of the rest the column. As before, water and heavy boiling impurities are withdrawn from the column bottom take-off outlet 10.

Also as before, polymerization inhibitors are added to the distillation column at feed points 14a (any inhibitors) and 14b (product compatible inhibitors only). Additionally, polymerization inhibitors may be added to the top of external intermediate condenser 16 through feed point 20. Because the inhibitors added through feed point 20 will be returned to the distillation column above side-draw take-off outlet 7, they must be compatible with the intended end use of the purified product.

Figure 4:
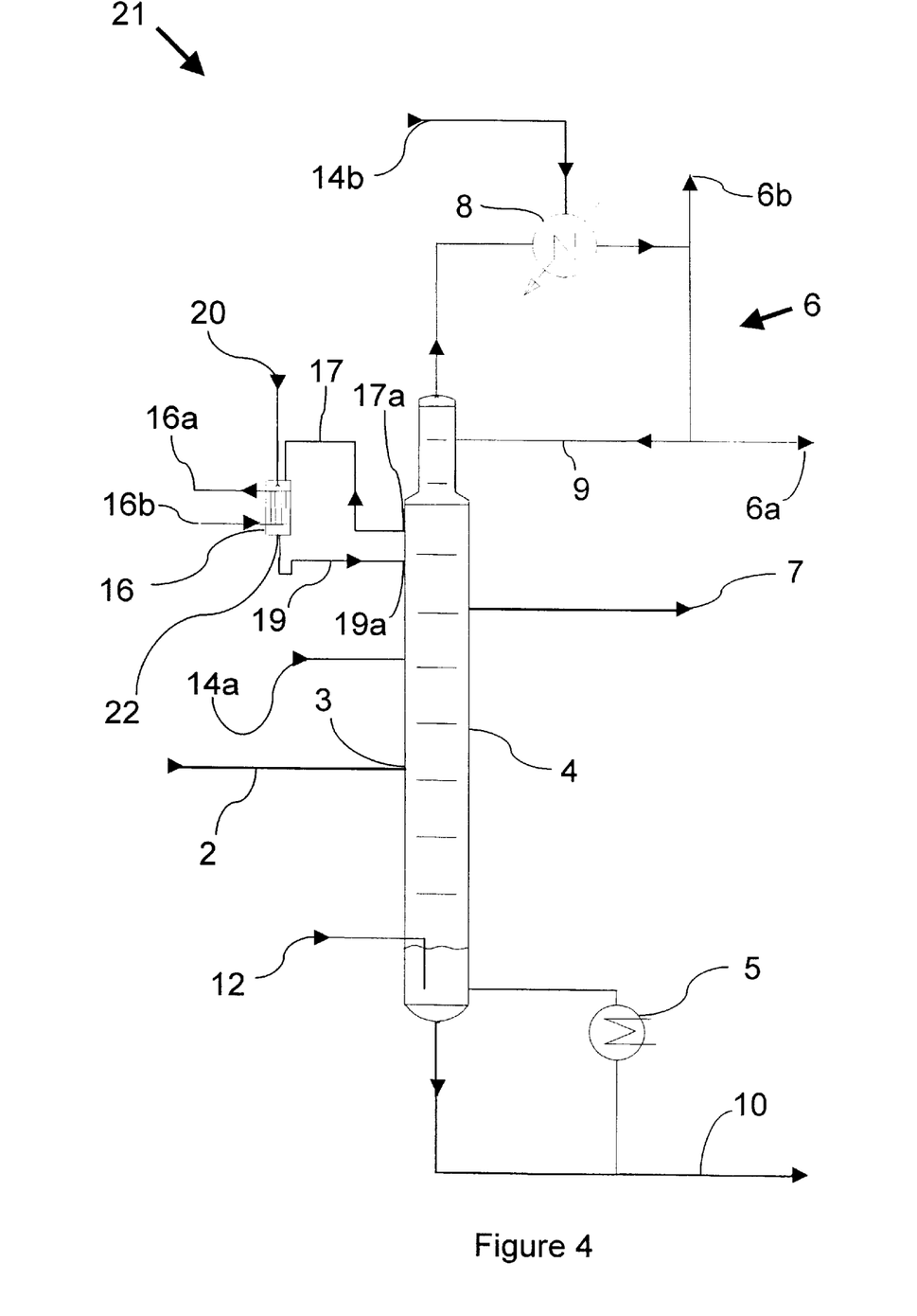
FIG. 4 is a schematic of a single-column distillation system of the invention with an elevated side external partial condenser and without reflux drum.

An alternate arrangement for the embodiment of FIG. 3 is represented in FIG. 4, where like numbers designate structures in common with FIGS. 1, 2 and 3.

Referring to FIG. 4, a single column distillation system comprising an intermediate external partial condenser lacking a reflux drum, severally designated 21, is shown. The system is essentially the same as is shown in FIG. 3, except that intermediate external partial condenser 16 is mounted at an elevation above reflux return point 19a, and draw 17 is routed above the top of intermediate partial condenser 16. There is no reflux drum attached to the condenser, and a liquid seal leg is present on outlet 22 for reflux return 19.

The arrangement shown in FIG. 4 obviates the need for long vapor and reflux return lines, an accumulator, or a reflux pump. There are several advantages to this arrangement. Capital and operating cost savings are realized by the elimination of the additional vapor and reflux piping, accumulator and pump. Safety benefits are obtained by eliminating the accumulator, as the inventory of hazardous compounds in the system is reduced. Also, a potential leakage point is eliminated by removal of the reflux pump. Thus, the arrangement of FIG. 4 is preferred.

Figure 5:
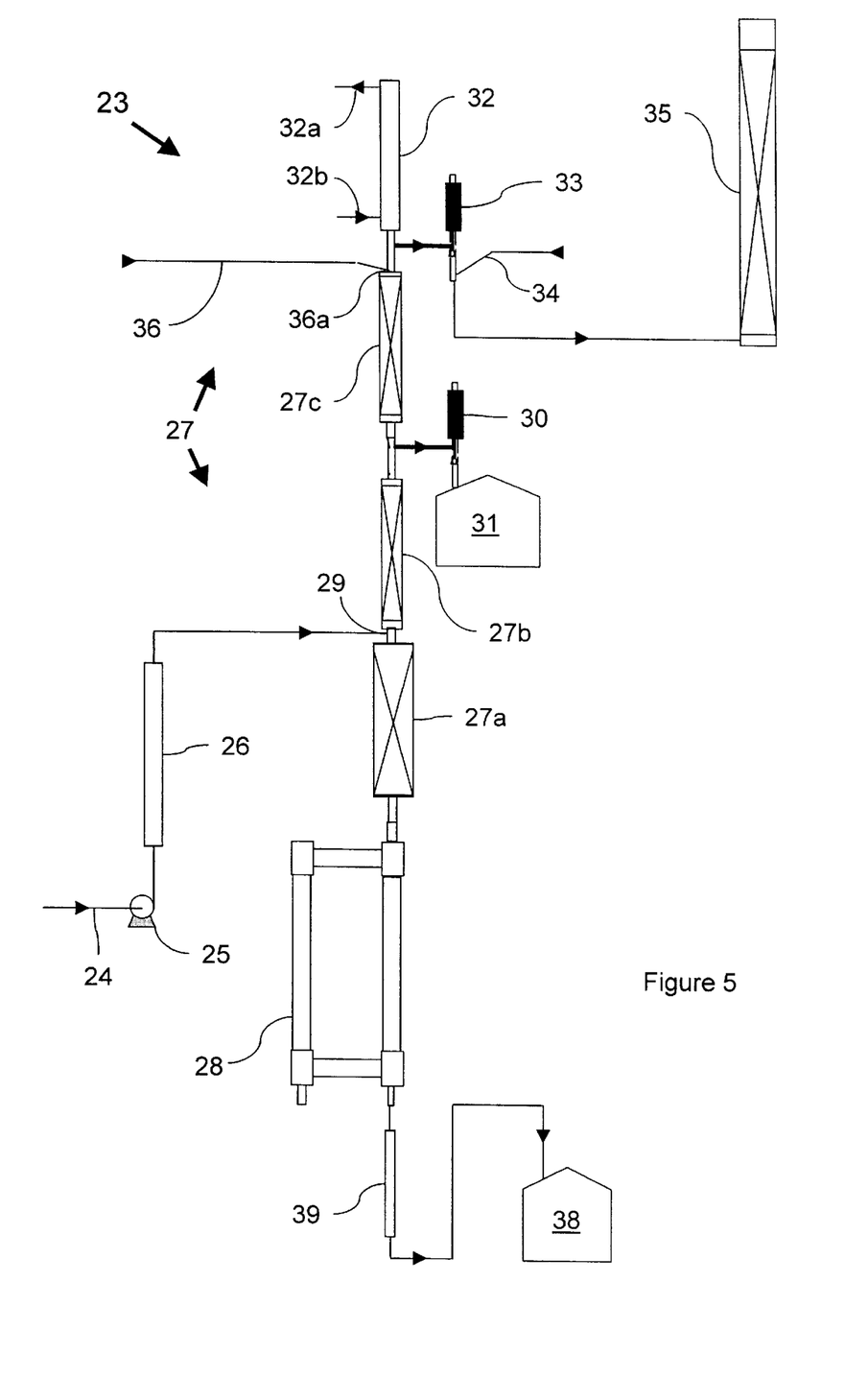
FIG. 5 is a schematic of a single column distillation system of the invention showing a stripping section and a rectifying section.

In a further embodiment, the present method is performed using a single column distillation system severally designated 23 as shown in FIG. 5. A crude dilute aqueous acrolein solution containing light-boiling impurities is pumped by pump 25 through preheating element 26 and transported to distillation column 27 by solution feed 24. Preferably, the crude acrolein solution is preheated to about 75–88° C. The crude solution is then introduced into the distillation column via crude product feed inlet 29.

From the lower end to the top end, distillation column 27 comprises, in order, stripping section 27a, rectifying section 27b, and light-boiling impurities distillation site 27c. Crude product feed inlet 29 is located directly above stripping section 27a.

Once in the distillation column, the crude acrolein solution falls through stripping section 27a and is heated to boiling by electrically heated reboiler 28, which is attached to the lower end of distillation column 27. Boiling the crude acrolein solution causes the solution to partially vaporize. The vapor travels up the distillation column, first passing through the stripping section 27a where acrolein and light-boiling impurities are separated from water.

Next, the acrolein and light-boiling impurities pass through the rectifying section 27b, where water associated with the acrolein is removed. Purified acrolein is then removed from the distillation column through liquid side-draw take-off outlet 30, which is located between rectifying section 27b and the light-boiling impurities distillation site 27c. The purified acrolein is collected in reservoir 31.

The light-boiling impurities continue to travel upward through light-boiling impurities distillation site 27c, where they are condensed in condenser 32, which is preferably a "cold finger" (e.g., closed top) condenser cooled with refrigerated anti-freeze solution circulated via inlet 32b and outlet 32a. The light-boiling impurities are removed from the distillation column through outlet 33 connected to nitrogen sweep 34, which is located between light-boiling impurities distillation site 27c and condenser 32. The function of the nitrogen sweep is to entrain/evaporate the lights distillate. The entrained lights distillate is transported to water quench column 35, which absorbs the nitrogen-entrained lights distillate to avoid discharge of these toxic components into the atmosphere.

Polymerization inhibitors that are acceptable for use with the product (e.g., hydroquinone dissolved in acrolein) may be added through feed 36 to feed point 36a, which is located above light-boiling impurities distillation site 27c.

All of the condensed overheads are returned to the top of the column as reflux. Column bottoms 38 receives water from the bottom of the stripping section 27a through cooling element 39. This water is substantially depleted of acrolein, but contains heavy-boiling impurities.

Single column distillation system 23 may further comprise auxiliary equipment to receive the distillate, side-draw product, and bottoms take-offs so as to avoid exposure of personnel to toxic materials.

Apart from the location of the side-draw take-off outlet as discussed above, it is understood that the configuration and dimensions of the single column distillation system are not critical as long as the desired purity of acrolein or propionaldehyde is obtained. Thus, column size, diameter, number and kind of stages and number of theoretical plates per stage may vary depending on the desired product purity and the scale of the purification to be undertaken.

For example, the distillation column may comprise a stripping section having between 3 and 8 theoretical plates between the feed and the heavy-boiling impurities distillation site; a rectifying section having between 4 and 10 theoretical plates between the feed and product side-draw points; and light-boiling impurities removal section having between 6 and 15 theoretical plates between the side-draw and the light-boiling impurities distillation site.

Smaller-scale distillations may be performed with a distillation column of approximately 20–40 mm; for example distillation a 38 mm diameter stripping section with 2 Sulzer EX packings plus 2 trays with downcomers (ca. 7 theoretical plates); a 22 mm diameter rectifying section with 2 Sulzer EX packings (ca. 6 theoretical plates); and a 22 mm diameter light-boiling impurities distillation site with 5 Sulzer EX packings (ca. 14 theoretical plates).

For large scale (e.g. industrial) uses, the distillation column diameter is preferably at least about 0.91 meter (3 feet) in diameter.

The invention will now be illustrated with the following non-limiting examples.

EXAMPLES 1–4

Laboratory-scale Distillations

Examples 1–4 were performed with the single column distillation system described in FIG. 2, with a 38 mm diameter stripping section consisting of 2 sections of Sulzer structured packing (equivalent to ~6 theoretical stages) above 2 sieve trays (with downcomers), a 20 mm diameter middle rectification section consisting of 6 sections of Sulzer structured packing 20 mm of Sulzer structured packing (equivalent to 18 theoretical stages), and a 20 mm diameter lights removal top section consisting of 6 sections of Sulzer structured packing 20 mm of Sulzer structured packing (equivalent to ~18 theoretical stages) above the side-draw take-off outlet. The water quench column was 38 mm in diameter.

The apparatus was also equipped with auxiliary equipment to receive the distillate, side-draw product, and bottoms take-offs, sampling points, and post-treatment to handle the materials in a manner to avoid exposure of personnel to toxic materials.

The polymerization inhibitor solution used was hydroquinone (100 ppm) dissolved in acrolein.

The distillation conditions and analysis of the acrolein product side-draw take-off, bottoms take-off, and quench column water are given in Table 1. These results show that acrolein was recovered and purified from an aqueous feed containing less than 3 wt % acrolein, and containing approximately 1.8 wt % acetaldehyde (on an water-free-basis), to yield a purified acrolein product taken as a side-draw take-off from the column. The side-draw take-off contained more than 95 wt % acrolein, and contained less than 0.6 wt % acetaldehyde.

From the material balance, the majority of the acetaldehyde was removed as the lights distillate. Based on the analysis of the quench water, the light-boiling impurities were concentrated in acetaldehyde (>65%) relative to the acrolein. This demonstrates the surprising result of how the side-draw achieves a lowest ratio of the light impurity (acetaldehyde) relative to the key component (acrolein) compared to the incoming feed, the lights distillate, or the bottoms.

TABLE 1

| | Ex. 1 | Ex. 2 | Ex. 3 | Ex. 4 |
|---|---|---|---|---|
| Distillate temperature (deg C.) | 28 | 28 | 35 | 46 (Vapor Distillate) |
| Reflux ratio | 150/1 | 150/1 | 100/1 | All Liquid refluxed; vapor distillate |
| Product Side-draw temperature (deg C.) | 55 | 55 | 55 | 51 |
| Reflux/Side-draw take-off split (ratio) | 15/1 | 15/1 | 15/1 | |
| Feed temperature (deg C.) | 82° C. | 79° C. | 80° C. | 86° C. |
| Reboiler temperature (deg C.) | 99.5° C. | 99.4° C. | 99.2° C. | 99.6° C. |
| Condenser coolant temperature (deg C.) | −5.0° C. | −5.0° C. | −5.0° C. | 13° C. |
| Residence time in reboiler | 1 h | 1 h | 1 h | 1 h |
| Aqueous Acrolein Feed | | | | |
| Feed flow (gal/hr) | 781.4 | 965.8 | 934.4 | 801.0 |
| Wt % Acrolein | 2.9085 | 2.9258 | 2.9030 | 2.6912 |
| Wt % Acetaldehyde | 0.0523 | 0.0529 | 0.0519 | .0585 |
| Hydroquinone Inhibitor | 100 ppm | 100 ppm | 100 ppm | 100 ppm |
| Acetaldehyde/Acrolein ratio | 0.0180 | 0.0181 | 0.0179 | .0217 |
| Top Inhibitor (hydroquinone solution in acrolein) | | | | |
| Feed flow (gal/hr) | 2.00 | 2.00 | 2.00 | 3.95 |
| Wt % Hydroquinone | 2.5 | 2.5 | 2.5 | 2.0 |
| Acrolein Product Side-draw Take-Off | | | | |
| Side-draw take-off flow (gal/hr) | 21.6 | 26.6 | 24.4 | 20.3 |
| Wt % Water | 4.0116 | 4.0323 | 2.8883 | 2.7400 |
| Wt % Acetaldehyde | 0.2126 | 0.5358 | 0.3968 | .0213 |
| Wt % Acrolein (calculated) | 95.78 | 95.43 | 96.71 | 97.00 |
| Acetaldehyde/Acrolein ratio | 0.0022 | 0.0056 | 0.0041 | 0.0002 |
| Bottoms Take-Off | | | | |
| Bottom take-off flow (gal/hr) | 784.4 | 940 | 923.7 | 774.8 |
| Wt % Acrolein | 0.0073 | 0.0522 | 0.0206 | .0026 |
| Wt % Acetaldehyde | 0.0020 | 0.0018 | 0.0008 | 0.0000 |
| Acetaldehyde/Acrolein ratio | 0.2740 | 0.0345 | 0.0388 | 0.0000 |
| Lights Absorbed into Quench Column Water | | | | |
| Acrolein/Acetaldehyde ratio in quench water | 0.18 | 0.35 | 0.53 | 2.13 |
| Acetaldehyde/Acrolein ratio | 5.55 | 2.84 | 1.88 | 0.47 |

EXAMPLES 5–7

Industrial Process Design Based On Simulations

In the following examples, process simulations (computer model) of the acrolein purification process were developed for use on Aspen Plus (version 10) process simulator. The simulation used the non-random two-liquid (NRTL) liquid activity coefficient model to calculate the vapor-liquid equilibria (VLE) for the simulations; NRTL parameters were fitted to published and proprietary mixture VLE data. The simulations were used to calculate the design and operating parameters for distillation columns to recover and purify acrolein.

The crude aqueous acrolein feed compositions given in Table 2 were used in all of the subsequent examples:

TABLE 2

| Feed Composition (wt %) | |
|---|---|
| Acrolein | 2.883 |
| Water | 96.476 |
| Formaldehyde | 0.050 |
| Acetaldehyde | 0.052 |
| Propionaldehyde | 0.002 |
| Allylic Alcohol | 0.453 |
| Acrylic Acid | 0.008 |
| Acetone | 0.005 |
| Others | 0.0707 |

EXAMPLE 5

Partial Vacuum To Improve Acrolein Product Purity

Example 5a in Table 3 below shows the simulation results for the side-draw column operated at atmospheric pressure; i.e., with the condenser at 760 mm Hg (absolute). Example 5b in Table 3 shows the simulation results for the same column, keeping the same distillate:feed ratio, reflux ratio, and acetaldehyde specification in the acrolein side-draw product, except that the column is operated under partial vacuum (condenser operating at 490 mm Hg (absolute)) with the attendant lower stage temperatures.

As can be seen by the simulation results, operating the acrolein purification under vacuum results in higher acrolein purities and recoveries as compared to atmospheric or above-atmospheric pressure operation.

TABLE 3

|  | Example 5a | Example 5b |
|---|---|---|
| Theoretical Stage number | | |
| Condenser | 1 | 1 |
| Top Tray | 2 | 2 |
| Side-draw | 16 | 16 |
| Feed | 22 | 22 |
| Reboiler | 30 | 30 |
| Top Condenser Pressure (mm Hg Abs) | 760 | 490 |
| Product Side-draw Stage Pressure (mm Hg Abs) | 921 | 651 |
| Top Condenser Temperature (deg C.) | 14.3 | −1.3 |
| Reflux Ratio | 159.15 | 159.15 |
| Acrolein Product Purity (wt %) | | |
| Acrolein | 96.34 | 96.97 |
| Acetaldehyde | 0.19 | 0.19 |
| Water | 3.19 | 2.58 |
| Others | 0.28 | 0.26 |
| Acrolein Recovery from Aqueous Feed (%) | 99.40 | 99.77 |

EXAMPLE 6

Side Condenser To Reduce Refrigeration Duty Of Top Condenser

Example 6a in Table 4 below shows the simulation results for the side-draw column operated under partial vacuum, using a refrigerated partial condenser to provide all of the reflux for the column. Example 6b shows the simulation results for the same column as used in Example 6a, maintaining the same acrolein product purities and recoveries, except that the column is provided with a side-condenser that can use conventional cooling media (e.g., cooling water or air cooling, up to ~40° C.) to provide the bulk of the reflux requirements in the acrolein-rich (middle) section of the column. This leaves the refrigerated condenser to provide reflux in the light-boiling impurities-rich (top) section of the column.

As can be seen by the simulation results, equipping the acrolein purification with a side-condenser between the top condenser and the product side-draw results in significantly lower (top) reflux ratios and refrigerated cooling duties. Since refrigerated cooling is energy-intensive, this results in more economical operation of the column.

TABLE 4

|  | Example 6a | Example 6b |
|---|---|---|
| Theoretical Stage number | | |
| Condenser | 1 | 1 |
| Top Tray | 2 | 2 |
| Side Condenser | none | 8 |
| Side-draw | 16 | 16 |
| Feed | 22 | 22 |
| Reboiler | 30 | 30 |

TABLE 4-continued

|  | Example 6a | Example 6b |
|---|---|---|
| Top Condenser Pressure (mm Hg Abs) | 490 | 490 |
| Top Condenser Temperature (deg C.) | 2.7 | 3.2 |
| Top Condenser Duty (Kcal/kg feed) | 18.44 | 1.69 |
| Side Condenser Duty (Kcal/kg feed) | — | 16.81 |
| Side Condenser Temperature (deg C.) | — | 41.7 |
| Reflux Ratio | 146.57 | 13.26 |
| Acrolein Product Purity (wt %) | | |
| Acrolein | 97.00 | 97.00 |
| Acetaldehyde | 0.19 | 0.19 |
| Water | 2.60 | 2.59 |
| Others | 0.21 | 0.21 |
| Acrolein Recovery from Aqueous Feed (%) | 99.40 | 99.40 |

Comparative Example 7

Acrolein Recoveries—Side-Draw vs. Conventional Acrolein Distillation

Example 7a in Table 5 below shows the simulation results for a conventional 3-column acrolein purification train, with the columns operated at atmospheric pressure. Example 7b in Table 5 shows the simulation results for a single column distillation system with both a side-draw take-off outlet and a side-condenser positioned above the liquid side-draw take-off outlet and below the top condenser, with the column operated at atmospheric pressure (760 mm Hg (absolute)). Example 7c shows the simulated results for the column of Example 7b operated under partial vacuum (490 mm Hg (absolute)). The columns in Examples 7b and 7c were operated in simulation to match the acrolein recovery and acetaldehyde impurity levels in the acrolein product of Example 7a.

As can be seen by the simulated results, equipping the single column distillation system with a side-draw take-off outlet achieves higher acrolein recoveries and reduced reboiler energy consumption than conventional multi-column distillation systems. Moreover, operating the present single-column system under a partial vacuum gives lower water concentrations in the final acrolein product. Furthermore, the temperatures to which the concentrated acrolein is subject to are lower, and residence times to which the concentrated acrolein is exposed at high temperatures are reduced. This results in less thermal degradation of acrolein, and its attendant fouling formation, as compared to conventional processes.

TABLE 5

|  | Example 7a | | | Ex. 7b | Ex. 7c |
|---|---|---|---|---|---|
|  | Azeo | Lights | Product | OVER ALL | Side-Draw | Side-Draw |
| Theoretical Stage number | | | | | |
| Condenser | 1 | 1 | 1 |  | 1 | 1 |
| Top Tray | 2 | 2 | 2 |  | 2 | 2 |
| Side Condenser | none | None | none |  | 5 | 8 |
| Side-draw | none | None | none |  | 16 | 16 |
| Feed | 8 | 9 | 4 |  | 22 | 22 |
| Reboiler | 16 | 24 | 5 |  | 30 | 30 |
| Top Condenser Pressure (mm Hg Abs) | 760 | 760 | 760 |  | 760 | 490 |
| Top Condenser Temperature | 40.0 | 20.0 | 52.3 |  | 14.3 | 3.2 |

TABLE 5-continued

| | Example 7a | | | | Ex. 7b | Ex. 7c |
|---|---|---|---|---|---|---|
| | Azeo | Lights | Product | OVER ALL | Side-Draw | Side-Draw |
| (deg C.) Top Condenser Duty (Kcal/kg feed) | 15.83 | 2.11 | 6.21 | | 3.05 | 1.69 |
| Side Condenser Duty (Kcal/kg feed) | | | | | 16.81 | 16.81 |
| Side Condenser Temperature (deg C.) | — | — | — | | 49.95 | 41.7 |
| Product Side-draw Pressure (mm Hg Abs) | — | — | — | | 921 | 651 |
| Reflux Ratio | 2.69 | 16.26 | 0.58 | | 24.44 | 13.26 |
| Reboiler Duty (Kcal/kg feed) | 24.79 | 2.53 | 6.09 | 33.41 | 29.22 | 27.65 |
| Acrolein Product Purity (wt %) | | | | | | |
| Acrolein | 94.15 | 96.11 | 96.34 | 96.34 | 96.34 | 97.00 |
| Acetaldehyde | 1.71 | 0.19 | 0.19 | 0.19 | 0.19 | 0.19 |
| Water | 3.20 | 3.37 | 3.18 | 3.18 | 3.19 | 2.59 |
| Others | 0.94 | 0.32 | 0.29 | 0.29 | 0.28 | 0.21 |
| Acrolein Recovery from Aqueous Feed (%) | 99.36 | 98.97 | 97.98 | 97.98 | 99.40 | 99.40 |

All documents referred to herein are incorporated by reference. While the present invention has been described in connection with the preferred embodiments of the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

We claim:

1. A method for purifying acrolein or propionaldehyde, comprising the steps of:
   1) providing a dilute aqueous solution comprising acrolein or propionaldehyde and light-boiling point impurities;
   2) providing a single column distillation system, comprising:
      i. a distillation column having a top condenser;
      ii. a crude product feed inlet on the distillation column;
      iii. a distillation site for the light-boiling point impurities above the crude product feed inlet;
      iv. a liquid side-draw take-off outlet for recovering purified acrolein or propionaldehyde located between the crude product feed inlet and the distillation site for the light-boiling point impurities; and
      v. a distillation site for the heavy impurities below the crude product feed inlet;
   3) introducing the dilute aqueous solution into the distillation column through the crude product feed inlet and distilling the dilute aqueous solution; and
   4) recovering purified acrolein or propionaldehyde through the liquid side-draw take-off outlet.

2. The method of claim 1, wherein the recovered purified product is acrolein.

3. The method of claim 1, wherein the distillation column is operated under a partial vacuum.

4. The method of claim 3, wherein the distillation column is operated is operated at a pressure of about 400 to about 650 mm Hg (absolute) as measured at the stage of the of side-draw take-off outlet.

5. The method of claim 4, wherein the single-column distillation system is operated is operated at a pressure of about 590 to about 650 mm Hg (absolute) as measured at the stage of the of side-draw take-off outlet.

6. The method of claim 1, wherein the purified acrolein or propionaldehyde obtained is at least about 95 wt % pure, with no more than 1% light-boiling impurities and no more than 4% water.

7. The method of claim 1, wherein the purified acrolein or propionaldehyde obtained is at least about 96% pure, with no more than 0.4% light-boiling impurities and no more than 3.0% water.

8. The method of claim 1, wherein the purified acrolein or propionaldehyde obtained is at least about 97% pure, with no more than 0.2% light-boiling impurities and no more than 2.6% water.

9. The method of claim 1, wherein the distillation column further comprises one or more vapor partial condensers intermediate between the liquid side-draw take off outlet and the top condenser, and the one or more vapor partial condensers produce a condensed liquid that is returned to the distillation column at one or more return points.

10. The method of claim 9, wherein the one or more vapor partial condensers are internal to the distillation column.

11. The method of claim 9, wherein the one or more vapor partial condensers are external to the distillation column.

12. The method of claim 11, wherein the one or more external vapor partial condensers are elevated above the one or more return points for the condensed liquid.

13. The method of claim 11, wherein the condensed liquid produced by the one or more external vapor partial condensers is discharged into a reflux drum prior to being returned to the distillation column.

14. The method of claim 1, wherein the distillation column further comprises one or more separation stages.

15. The method of claim 14, wherein the separation stages include a stripping stage and a rectifying stage.

16. The method of claim 1, further comprising the step of adding at least one polymerization inhibitor to the single column distillation system after introducing the dilute aqueous solution into the distillation column.

17. The method of claim 16, wherein the at least one polymerization inhibitor is added to the distillation column at a point between the side-draw take-off outlet and the crude product feed inlet.

18. The method of claim 16, wherein the at least one polymerization inhibitor comprises hydroquinone or a derivative of hydroquinone.

19. The method of claim 18, wherein the at least one polymerization inhibitor comprises the methyl ether of hydroquinone.

20. The method of claim 16, wherein the at least one polymerization inhibitor comprises phenothiazine or a derivative of phenothiazine.

21. The method of claim 16, wherein the at least one polymerization inhibitor comprises a mixture of polymerization inhibitors.

22. The method of claim 21, wherein the mixture of polymerization inhibitors includes a compound selected from the group consisting of hydroquinone, derivatives of hydroquinone, phenothiazine or derivatives of phenothiazine.

* * * * *